(12) United States Patent
Ahlers et al.

(10) Patent No.: US 9,976,970 B2
(45) Date of Patent: May 22, 2018

(54) SOURCE WELL DIVIDER SUITABLE FOR CURVED SOURCE WELLS

(71) Applicant: Vega Americas, Inc., Cincinnati, OH (US)

(72) Inventors: Shawn Gregory Ahlers, Mason, OH (US); David Williams, Fairfield, OH (US)

(73) Assignee: Vega Americas, Inc., Cincinnati, OH (US)

( * ) Notice: Subject to any disclaimer, the term of this patent is extended or adjusted under 35 U.S.C. 154(b) by 0 days. days.

(21) Appl. No.: 15/104,155

(22) PCT Filed: Dec. 12, 2014

(86) PCT No.: PCT/US2014/069883
§ 371 (c)(1),
(2) Date: Jun. 13, 2016

(87) PCT Pub. No.: WO2015/089347
PCT Pub. Date: Jun. 18, 2015

(65) Prior Publication Data
US 2016/0313264 A1  Oct. 27, 2016

Related U.S. Application Data

(60) Provisional application No. 61/915,641, filed on Dec. 13, 2013.

(51) Int. Cl.
| | | |
|---|---|---|
| *G01V 5/00* | (2006.01) | |
| *G01N 23/10* | (2018.01) | |
| *G01F 23/288* | (2006.01) | |

(52) U.S. Cl.
CPC ........... *G01N 23/10* (2013.01); *G01F 23/288* (2013.01); *G01N 2223/637* (2013.01)

(58) Field of Classification Search
CPC ................................ G01N 23/10; G01N 9/24
(Continued)

(56) References Cited

U.S. PATENT DOCUMENTS 3,693,648 A * 9/1972 Sassin ........................ F16L 9/19
137/375
3,941,654 A * 3/1976 Tarasuk ................. G21C 3/322
376/243

(Continued)

FOREIGN PATENT DOCUMENTS

| EP | 2 169 389 A1 | 3/2010 |
|---|---|---|
| WO | 2010032064 A1 | 3/2010 |

OTHER PUBLICATIONS

U.S. Appl. No. 14/069,883, International Search Report and Written Opinion, dated Mar. 2, 2015.

(Continued)

*Primary Examiner* — Taeho Jo
(74) *Attorney, Agent, or Firm* — Wood Herron & Evans LLP (57) ABSTRACT

A source well divider for use with a nuclear level gauge on a process vessel 24, permits the insertion of multiple radiation sources 12 in the source well. The divider includes a plurality of lengths of flexible interlocked metallic tubing 18, each length extending into the source well 22 from a nozzle in the vessel 24, forming a plurality of independent sub-wells each permitting the installation of an independently cabled radiation source 12 into the source well.

6 Claims, 8 Drawing Sheets

(58) Field of Classification Search
USPC .......................................................... 250/256
See application file for complete search history.

(56) References Cited

U.S. PATENT DOCUMENTS

| | | | | |
|---|---|---|---|---|
| 3,958,120 | A * | 5/1976 | Ward | G01N 23/18 378/181 |
| 3,994,173 | A * | 11/1976 | Ward | F22B 37/003 250/497.1 |
| 4,046,632 | A * | 9/1977 | Puchelt | F16L 13/02 376/203 |
| 4,580,052 | A * | 4/1986 | Hoffman | G01F 23/288 250/357.1 |
| 4,678,630 | A * | 7/1987 | King | G21C 3/33 376/438 |
| 4,917,853 | A * | 4/1990 | Feurgard | G21C 17/108 376/203 |
| 5,084,002 | A * | 1/1992 | Liprie | A61N 5/1027 600/3 |
| 5,105,876 | A * | 4/1992 | Burack | F22B 37/003 165/11.2 |
| 5,333,502 | A | 8/1994 | Clark, Jr. et al. | |
| 5,611,391 | A | 3/1997 | Hyp | |
| 5,782,742 | A * | 7/1998 | Crocker | A61N 5/1002 600/3 |
| 2001/0015233 | A1 * | 8/2001 | Herman | B21C 37/124 138/135 |
| 2004/0251416 | A1 | 12/2004 | Baldwin et al. | |
| 2006/0049345 | A1 * | 3/2006 | Rao | G01T 1/20 250/269.1 |
| 2010/0080352 | A1 * | 4/2010 | Cahill | G01F 23/288 378/54 |
| 2013/0087715 | A1 | 4/2013 | Cahill | |

OTHER PUBLICATIONS

Anonymous: "Metal Hose Products Featuring HOS TEC Barnd Metal Hose", Dec. 31, 2018, pp. 1-20, XP055375828; Retrieved from Internet: URL: http://products.kuriyama.com/asset/Kuriyama-Metal-Hose-Cat-20-pg-6-20-2008.pdf (retrieved on May 24, 2017].

* cited by examiner

INTERLOCKED
FLEXIBLE
METAL
TUBING

FIG. 6

SOURCE WELL DIVIDER SUITABLE FOR CURVED SOURCE WELLS

CROSS REFERENCE TO RELATED APPLICATION

This application claims benefit of U.S. Provisional Patent Application Ser. No. 61/915,641 filed Dec. 13, 2013, which is hereby incorporated herein in its entirety.

FIELD OF THE INVENTION

The present invention relates to nuclear level sensing gauges used in industrial process control and similar environments.

BACKGROUND OF THE INVENTION

Figure 1:
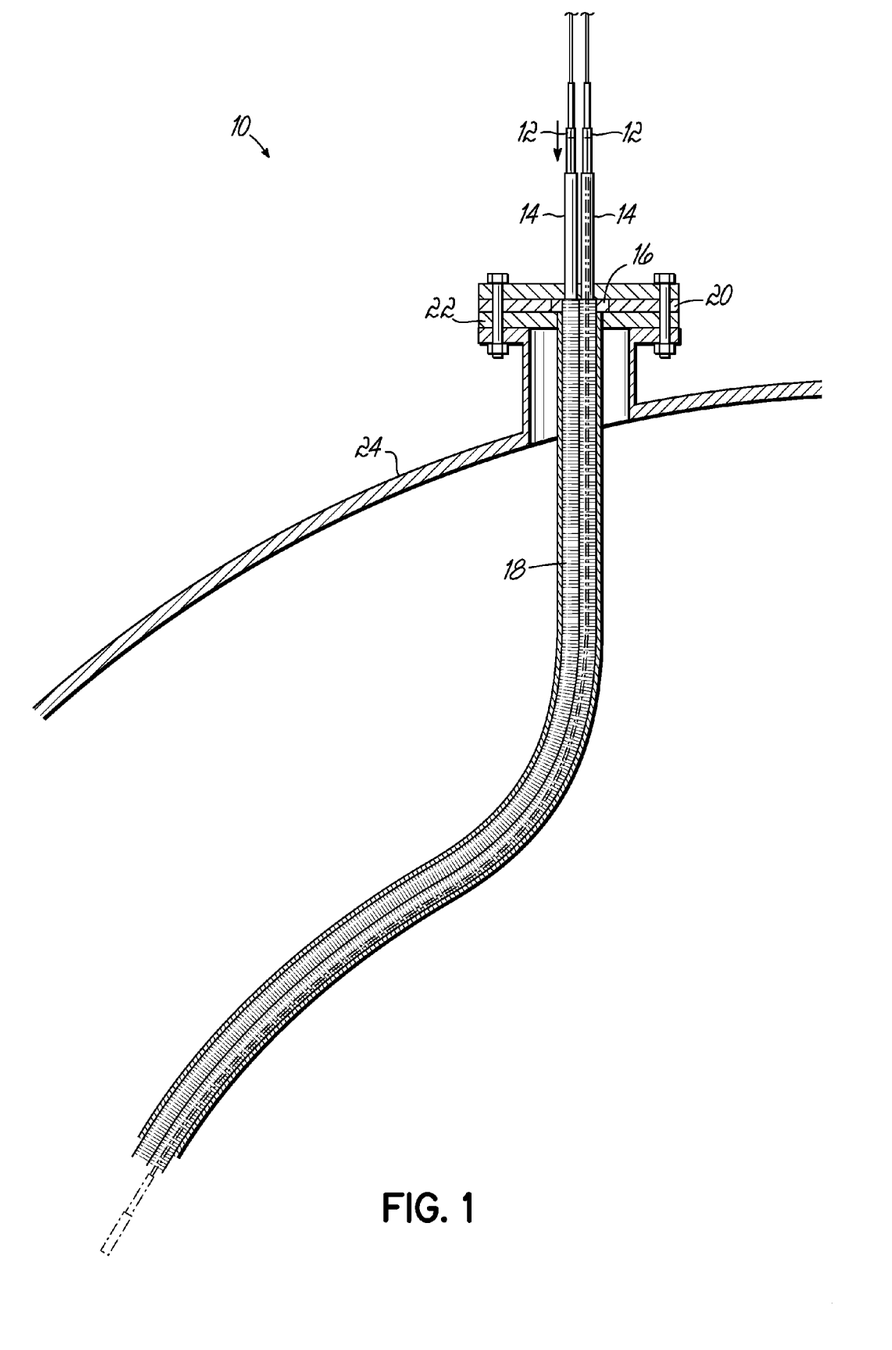
FIG. 1 is a cross-sectional view of a source well assembly 10 and process vessel utilizing principles of the present invention.

Nuclear density gauges are often used to measure liquids (the term liquid, when used in this application for patent, includes slurries) in a vessel at places such as oil refineries. As illustrated in FIG. 1, a nuclear density gauge often includes a source well that extends into the vessel from the top thereof, so that a nuclear source can be installed into the source well and then radiation from the source can be detected, e.g. with a scintillation detector, from outside of the vessel to determine factors such as level and density of the liquid in the vessel. When radiation leaves the source, the amount reaching the detector aligned with the source decreases as the distance between them increases, even if there is only a vacuum between them. When passing through a liquid in a vessel, the mass of the liquid absorbs some of the radiation. In addition to the liquid, if the source, the detector, or both, are located outside the vessel, the radiation must also pass through at least one of the vessel walls. Since the absorption of the radiation by the walls is constant, and the distance between a source and a detector is constant, the amount of radiation reaching the detector is indicative of the presence of liquid between the source and detector, and of the density of the liquid it passes through. As the density of the liquid changes, the amount of radiation reaching the detector changes. The greater the density of the liquid, the less radiation reaches the detector. The detector typically provides density measurement in the form of a current output.

It should also be noted, that to keep a detector cool, and make it easier to maintain, detectors are almost always located outside the vessel. The source, however, can be durably packaged, and more easily placed inside the vessel. A source well enables the source to be placed within the vessel, hanging on the end of a cable, and separated from the liquid. This allows maintenance, calibration and testing of the source on an appropriate schedule by withdrawing the source from the well using the cable.

In some installations, multiple sources are placed in the well at varying heights, to allow measurement of level and density at multiple points within the vessel for better process control. Each source is typically hung in the well on its own cable so that the sources can be separately withdrawn for maintenance, and their heights can be separately controlled.

SUMMARY OF THE INVENTION

A challenge arises with source wells used with multiple sources, in that the cables on which the sources hang can become entangled and make it difficult to accurately position the sources in the well, as well as hinder the separate extraction and maintenance of the sources. These problems are exacerbated when the source well 18 is curved along its length, like the one shown in FIG. 1. Curved source wells are necessary for some implementations; for example, vessels with broad curved shoulders like vessel 24 seen in FIG. 1 require the source well nozzle to be positioned far from a vessel wall. In such applications, a curved well can be used to bring the radiation sources closer to a vessel wall, and thus increase the amount of radiation that reaches the external detectors and create more accurate readings.

In accordance with principles of the present invention, the difficulties with using multiple sources, particularly in a curved source wells, are overcome by the use of a flexible source well divider, which comprises several, e.g. four, lengths of flexible interlocked metallic tubing that extend into the source well and form plural independent wells for placement of each of the independent sources.

In particular embodiments describe herein, the source well is curved along its length, the plural lengths of tubing being curved in conformity to the source well along their lengths. The lengths of tubing extend for at least a portion of the length of the source well, with one length of tubing extending for the entire length of the source well. The interlocked metallic tubing itself is comprised of interlocking strips coiled in a spiral fashion.

The above and other objects and advantages of the present invention shall be made apparent from the accompanying drawings and the description thereof.

DETAILED DESCRIPTION

FIG. 1 is a cross-sectional view of a source well assembly 10 utilizing principles of the present invention, mounted to a vessel 24 incorporating a vessel nozzle having clamped thereto a source well 22, flexible hose flange 20 and attached flexible hoses 18 each aligned with a source holder having sub-well openings 14, so that source holders 12 can be lowered on their respective cables into each sub-well opening 14 and related tubing section 18 to an appropriate position inside the vessel within the source well.

Figure 2A:
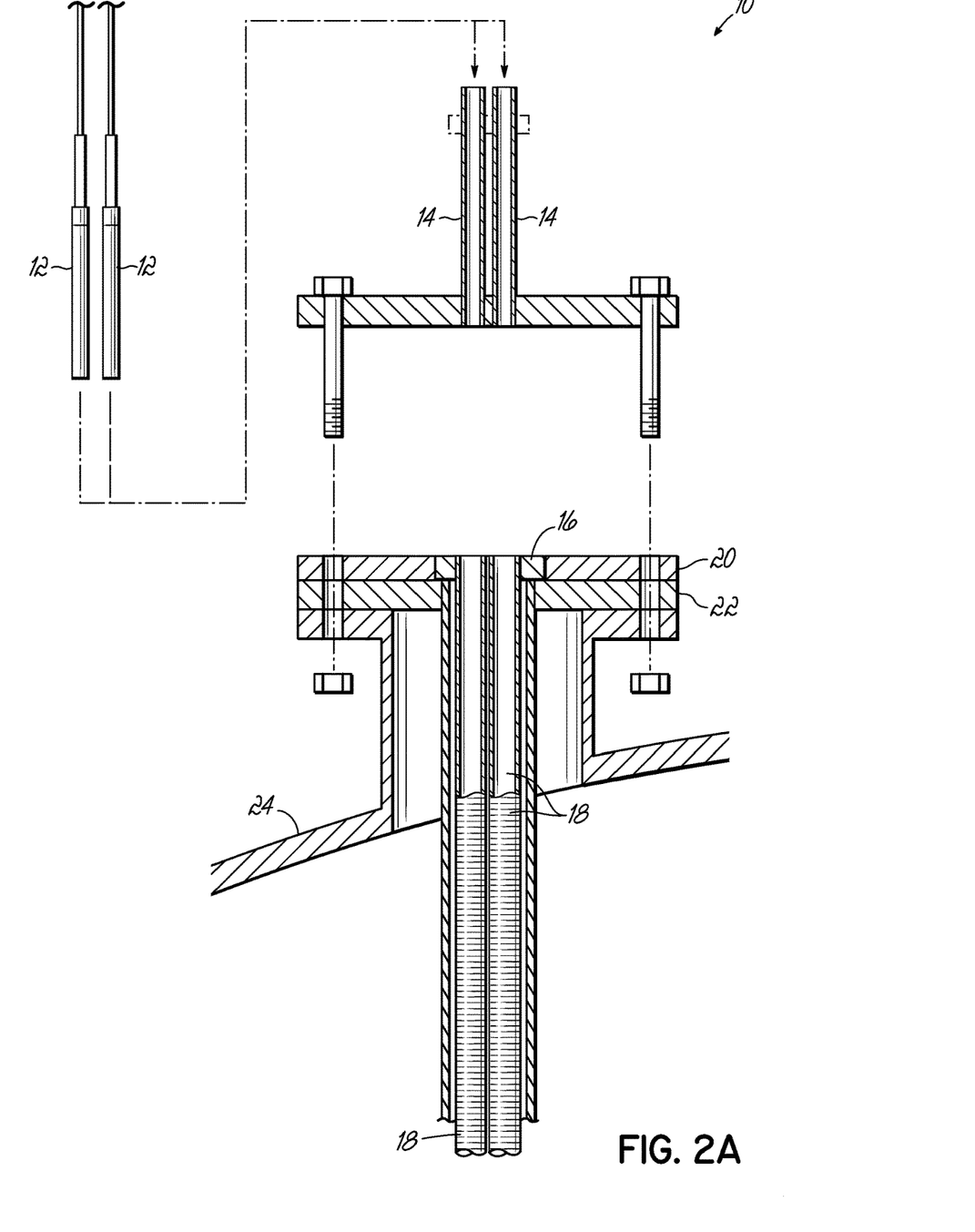
FIGS. 2A, 2B and 2C illustrates the manner in which the source well assembly of FIG. 1 is assembled, and source holders are lowered on cables into the flexible hoses in the assemblage.

FIG. 2A illustrates the assembly of the source holder 12 to the assembly of the source holder (which supports sub-well openings 14), flexible hose flange 20, flexible hoses 18, source well and flange 22, and vessel nozzle in the vessel wall 24. As seen in FIG. 2A the flexible hoses 18 are mounted to a fitting 16 which inserts into the flexible hose flange 20 to retain the hoses 18 positioned in the source well.

Figure 2B:
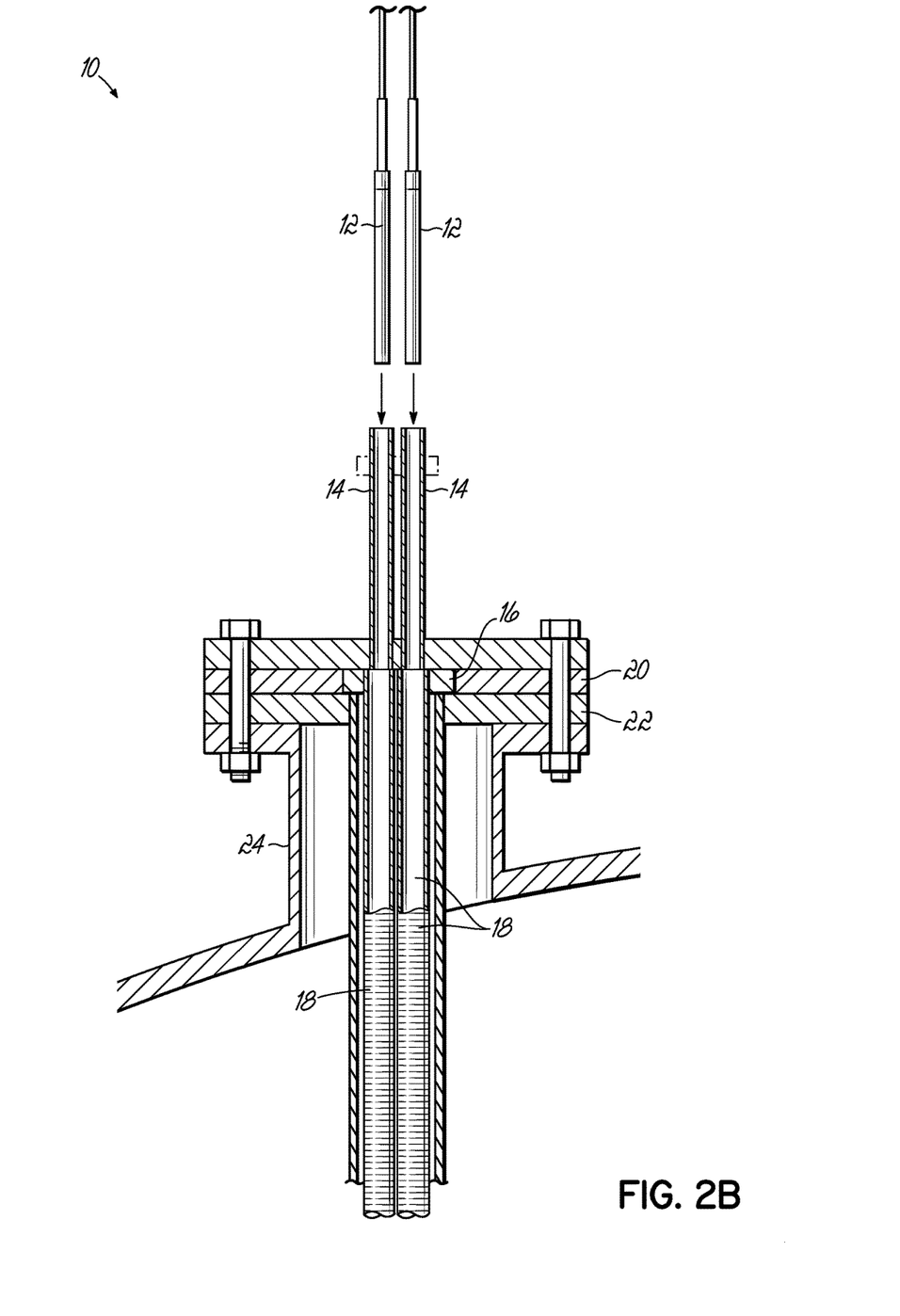

FIG. 2B illustrates the vertical insertion of the source holders 12 into the completed assembly of the source holder and its well openings 14. The top plate is mounted in a stack including the flexible hose flange 20 and source well flange 22. As thus assembled the flexible hoses 18 are supported by the end flange 16 in the source well, and the source well is supported by flange 22 on the vessel nozzle in the vessel wall 24.

Figure 2C:
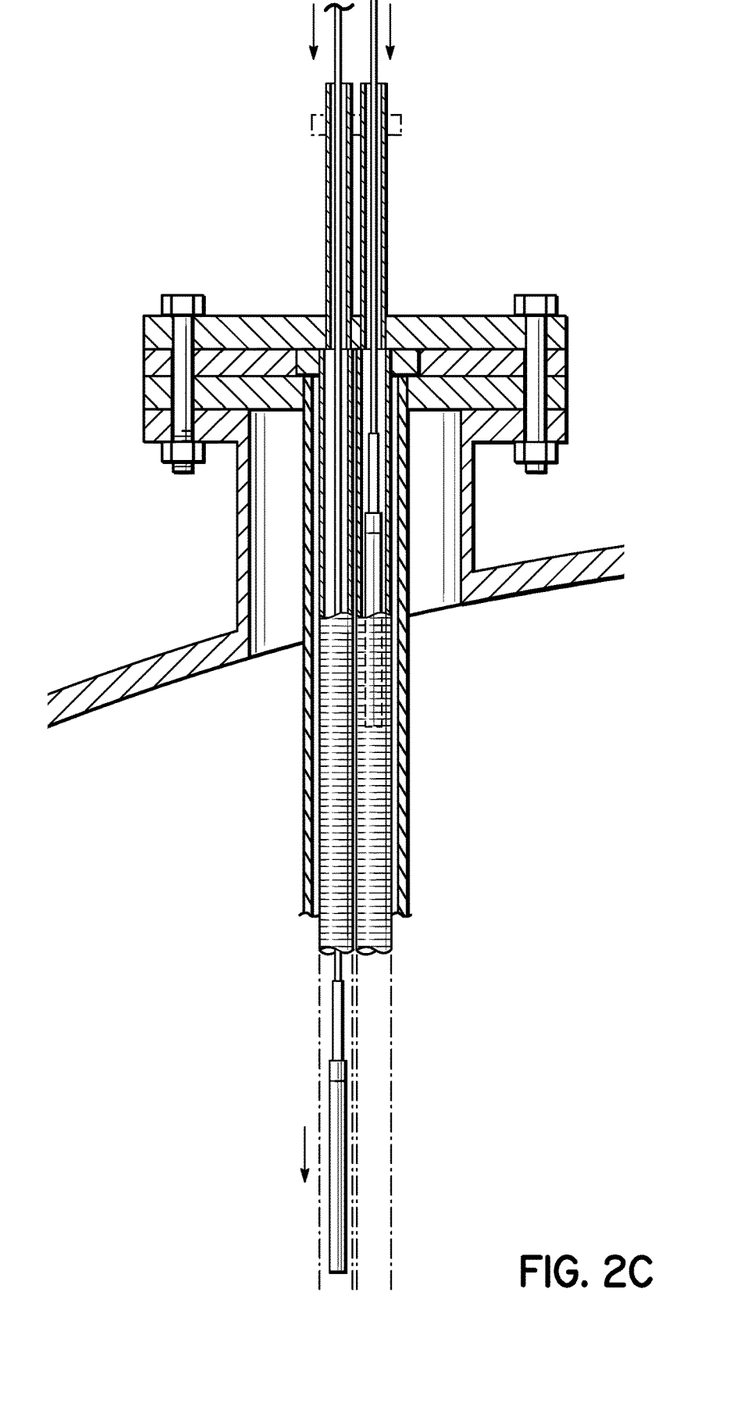

FIG. 2C illustrates the manner in which the source holders 12 are lowered on the cables into the flexible hoses 18 in the assemblage described above.

Figure 3:
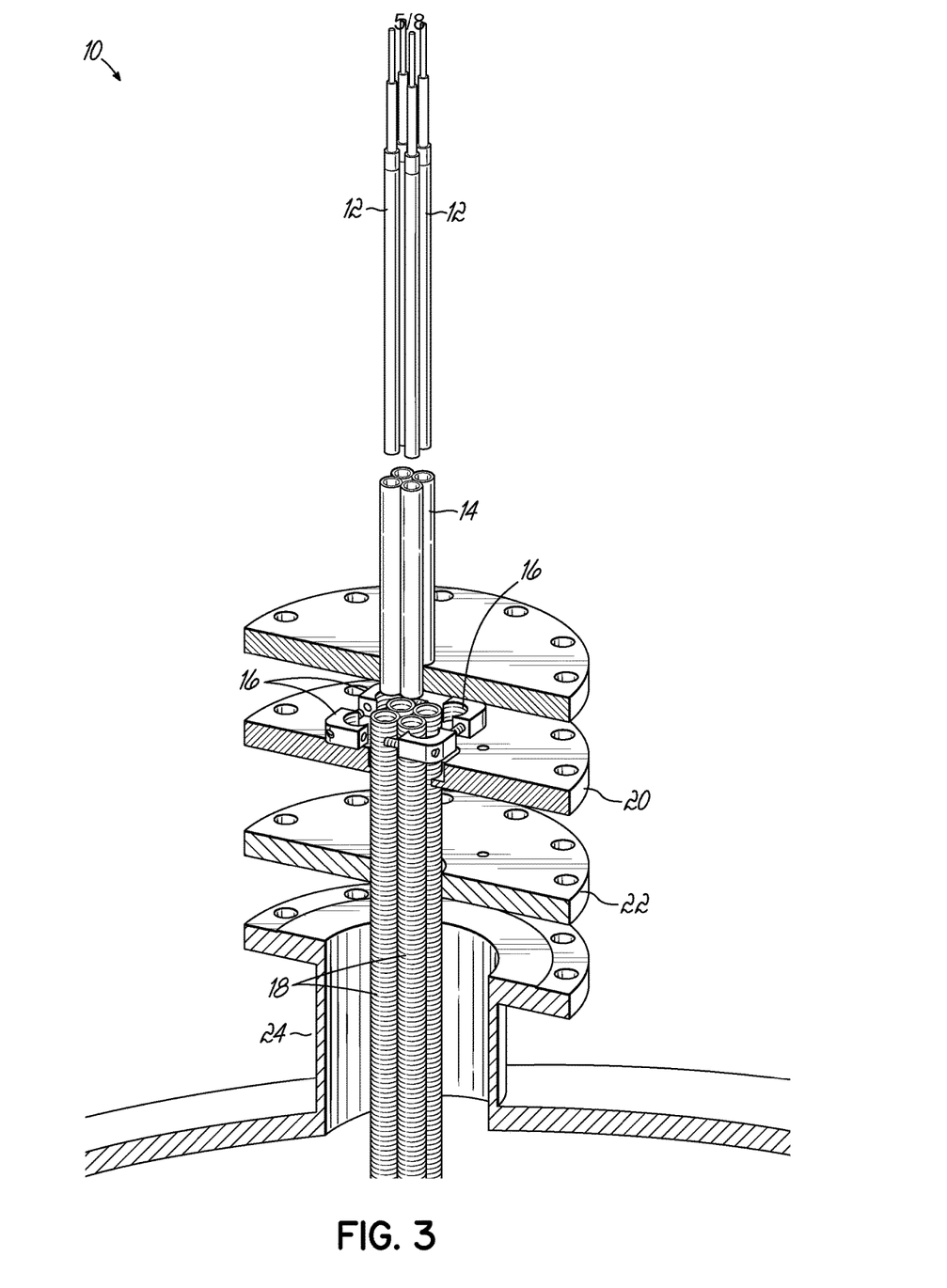
FIG. 3 is a disassembled perspective view of the assembly FIG. 1.

FIG. 3 is a disassembled perspective view of the assembly discussed above. As shown in FIG. 3, a source well assembly 10 is built to receive a source carrier 12 which hangs from an extending cable. The sources are each suspended on the cables from the four source sub-well openings 14 integrally mounted on the source holder. The source holder is clamped to flexible hose flange 20, which includes the flexible hose fitting 16 that clamps to the four flexible hoses 18 that extend into the source well 22. The source well 22 flange bolts to a mating flange on the vessel nozzle which is mounted to the top wall of the vessel 24.

The flexible hoses 18 act as dividers which extend into the source well 22 and provide independent pathways for the plural sources 12 to hang into the source well, controlling the source and cable around bends in the source well to prevent entanglement of the sources and cables with each other, thus ameliorating the difficulties explained above.

Figure 4:
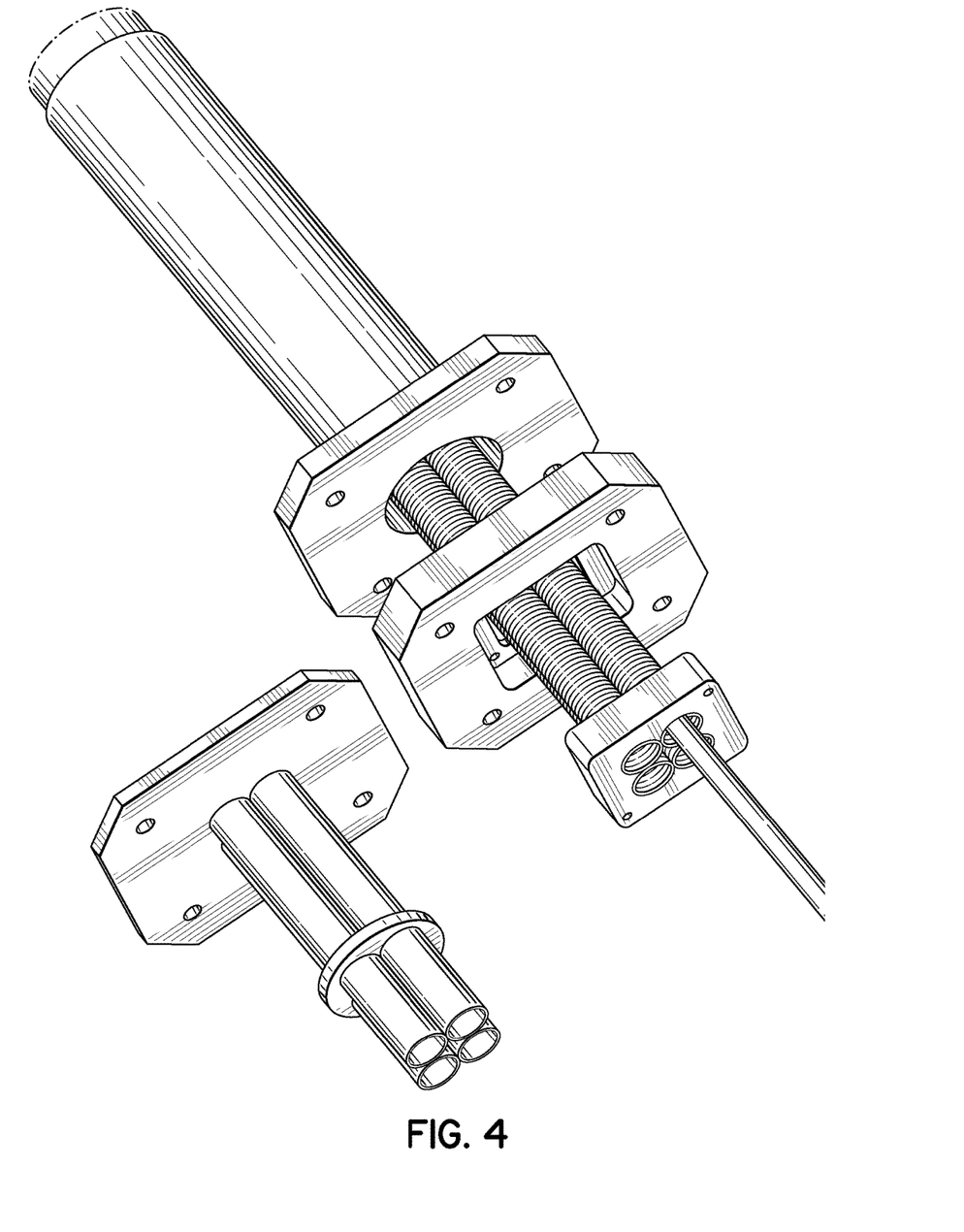
FIG. 4 is an alternate disassembled perspective view of the assembly of FIG. 1.

FIG. 4 is an embodiment of the invention in a disassembled state.

Figure 5:
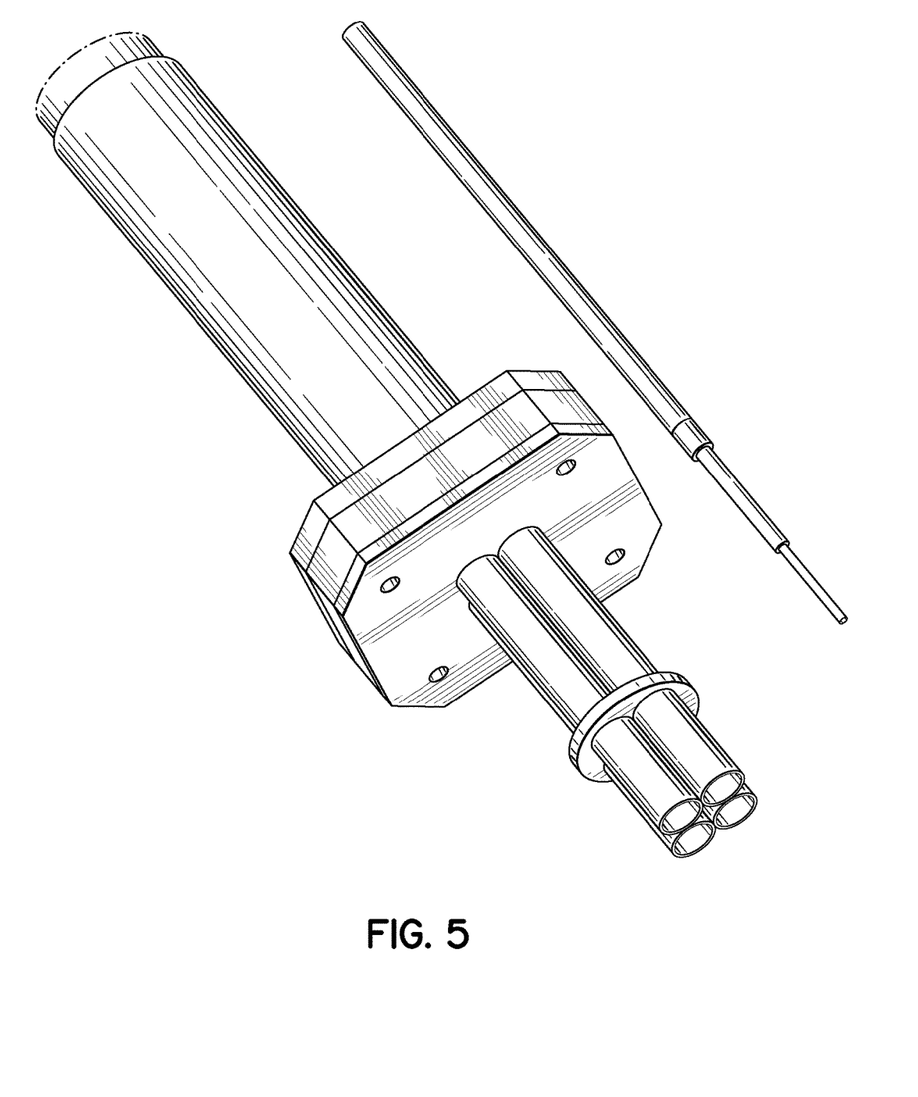
FIG. 5 is an assembled perspective view of the assembly of FIG. 1.

FIG. 5 is the embodiment of FIG. 4 when assembled.

Figure 6:
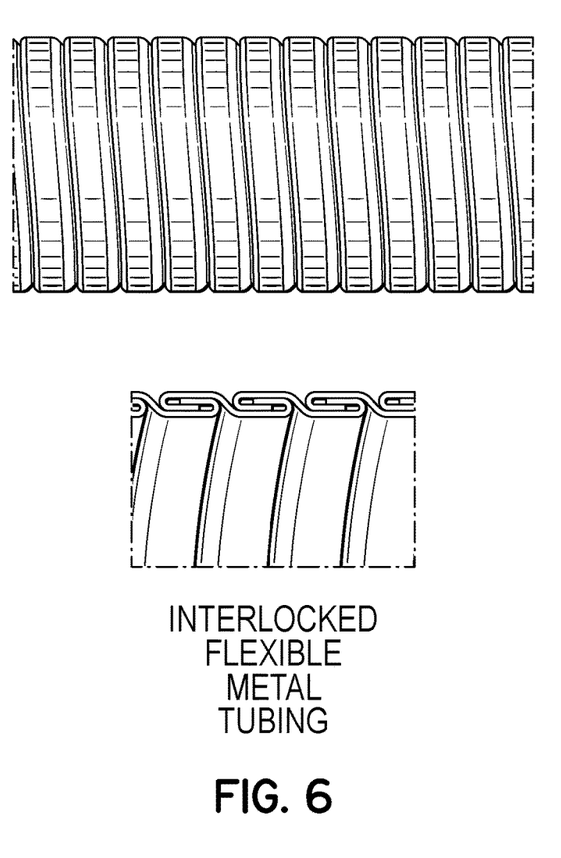
FIG. 6 is an illustration of the construction details of the flexible hoses used in the assembly of FIG. 1.

FIG. 6 is a cross section and perspective illustration of the interlocked flexible metal tubing used for hoses 18. The tubing wall is formed of a spiral wound interlocking metal strip, with the cross section of the interlocking strip shown in FIG. 6. The interlocked metal tubing generally comprises interlocking strips of between 0.018 to 0.020 inch thickness in galvanized or stainless steel, coiled in spiral fashion into a flexible tube, as seen in FIG. 6.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

The invention claimed is:

1. A source well divider installed within a source well of a nuclear level gauge on a process vessel, comprising:
   a process vessel having an interior and exterior,
   a source well extending into the interior of the process vessel such that a nuclear source may be installed into the interior of the process vessel inside of the source well, and
   a divider permitting the insertion of multiple radiation sources in the source well, comprising a plurality of lengths of flexible interlocked metallic tubing, each length extending into the source well from a nozzle in the vessel and into the interior of the process vessel, and forming a plurality of independent wells each permitting the installation of an independently cabled radiation source into the source well.

2. The divider of claim 1 wherein the source well is curved along its length, the plural lengths of tubing being curved in conformity to the source well along their lengths.

3. The divider of claim 1 wherein the lengths of tubing extend for a portion of the length of the source well.

4. The divider of claim 1 wherein at least one length of tubing extends for the entire length of the source well.

5. The divider of claim 1 comprising four lengths of interlocked metallic tubing.

6. The divider of claim 1 wherein the interlocked metallic tubing comprises interlocking strips coiled in spiral fashion.

* * * * *